United States Patent
Shifrin et al.

(10) Patent No.: US 7,776,082 B2
(45) Date of Patent: Aug. 17, 2010

(54) METHOD AND EXTRAVENOUS CORRECTOR FOR SIMULTANEOUS REPAIR OF MULTIPLE INCOMPETENT VALVES

(75) Inventors: Edward Shifrin, Raanana (IL); Gennady S. Nichelshpur, Haifa (IL); Andrew Nicolaides, Nicosia (CY); Wesley S. Moore, Los Angeles, CA (US)

(73) Assignee: Valcor Ltd., Raanana (IL)

( * ) Notice: Subject to any disclaimer, the term of this patent is extended or adjusted under 35 U.S.C. 154(b) by 716 days.

(21) Appl. No.: 10/545,938

(22) PCT Filed: Feb. 28, 2003

(86) PCT No.: PCT/US03/06188

§ 371 (c)(1), (2), (4) Date: Aug. 9, 2007

(87) PCT Pub. No.: WO2004/078073

PCT Pub. Date: Sep. 16, 2004

(65) Prior Publication Data

US 2007/0293877 A1 Dec. 20, 2007

(51) Int. Cl.
*A61F 2/06* (2006.01)
(52) U.S. Cl. .................. 623/1.24; 606/151; 606/153
(58) Field of Classification Search ............... 623/1.24, 623/1.22, 1.35; 606/151–156, 37
See application file for complete search history.

(56) References Cited

U.S. PATENT DOCUMENTS

| | | | |
|---|---|---|---|
| 3,726,279 A * | 4/1973 | Barefoot et al. ............ 606/151 |
| 5,147,389 A | 9/1992 | Lane | |
| 5,476,471 A | 12/1995 | Shifrin et al. | |
| 5,540,701 A * | 7/1996 | Sharkey et al. ............ 606/153 |
| 5,906,206 A | 5/1999 | Shaw et al. | |
| 6,409,750 B1 * | 6/2002 | Hyodoh et al. ............ 623/1.1 |
| 6,517,558 B2 * | 2/2003 | Gittings et al. ............ 606/153 |
| 6,802,858 B2 * | 10/2004 | Gambale et al. ........... 623/1.35 |

FOREIGN PATENT DOCUMENTS

WO  WO 96/38090 A1  3/1996
WO  WO 97/40755 A1  11/1997

* cited by examiner

*Primary Examiner*—Corrine M McDermott
*Assistant Examiner*—Tiffany Shipmon
(74) *Attorney, Agent, or Firm*—William J. Sapone; Coleman Sudol Sapone P.C.

(57) ABSTRACT

A method and device for repairing incompetent venous valves and more specifically relates to repair method and an implantable support device—extravenous corrector (3), which is positionable about a dilated veins of the Sapheno-Femoral Junction (SFJ) (1) with the aim to apply an external compression force on the insufficient veins of SFJ and especially in the area of the venous valves. There are proposed several embodiments of a extravenous corrector for external correction of insufficient valves in venous junctions. The corrector is adapted to be placed immediately around the junction with venous valves, in abutting contact with its external area. The extravenous corrector comprises a central support member (11) and at least three band lengths (13, 15, 17), connected to the member, adapted for placement around at least two veins of the venous junction in area of location of their insufficient valves, these band lengths possessing different rigidity and compressing force in direction from their proximal end to the distal end.

21 Claims, 11 Drawing Sheets

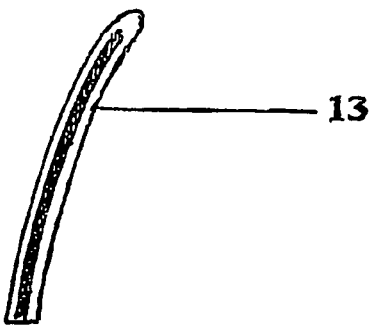

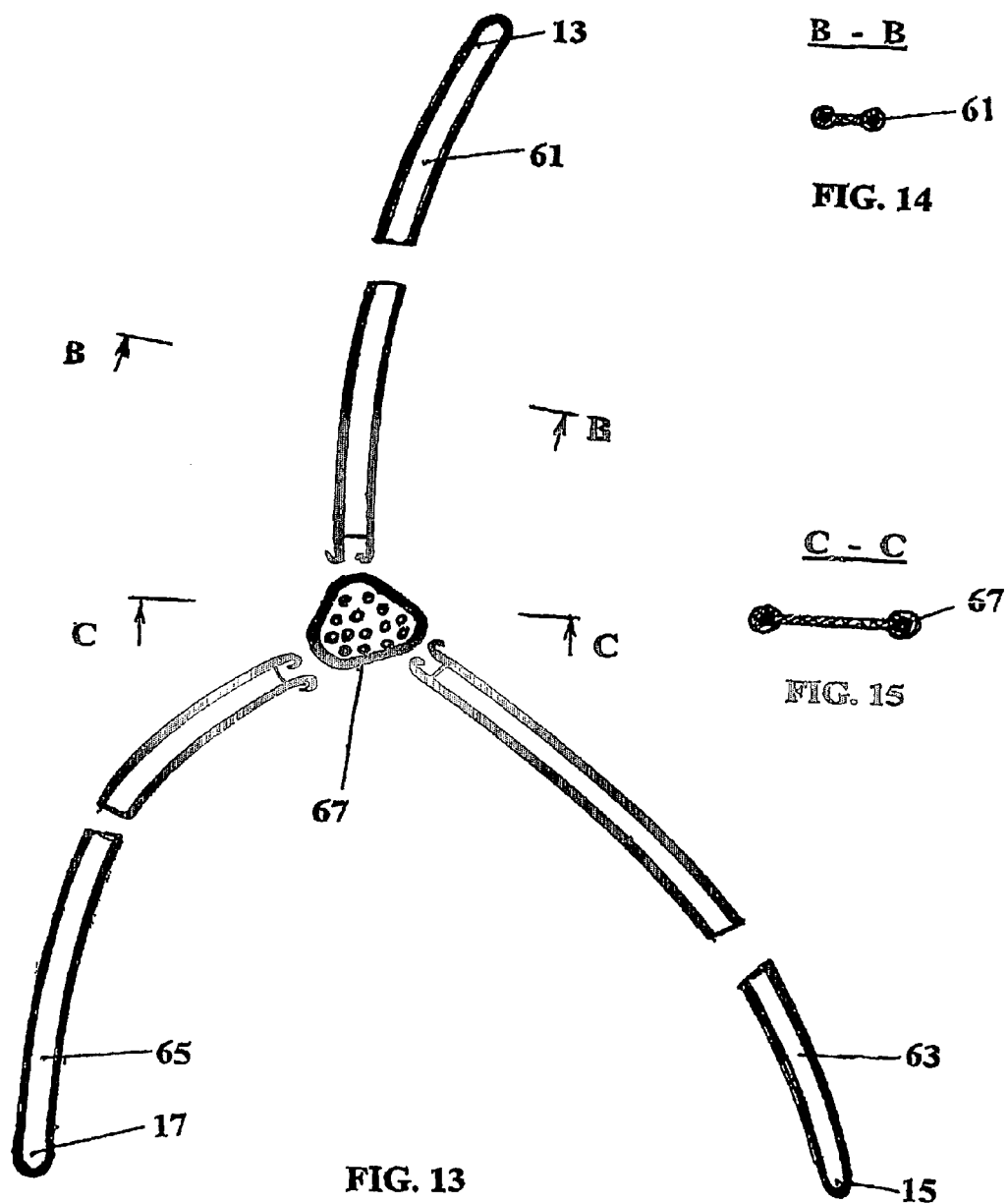

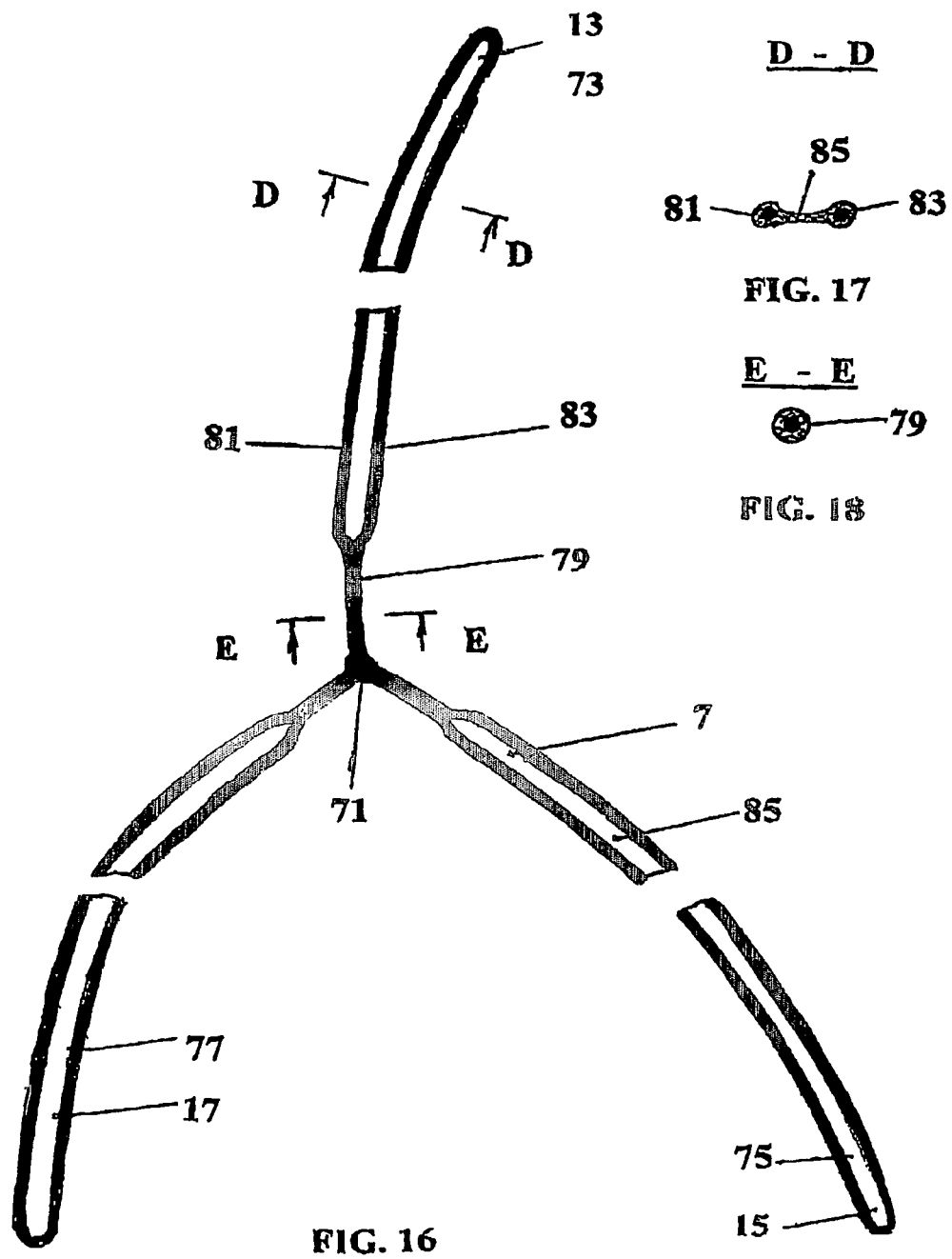

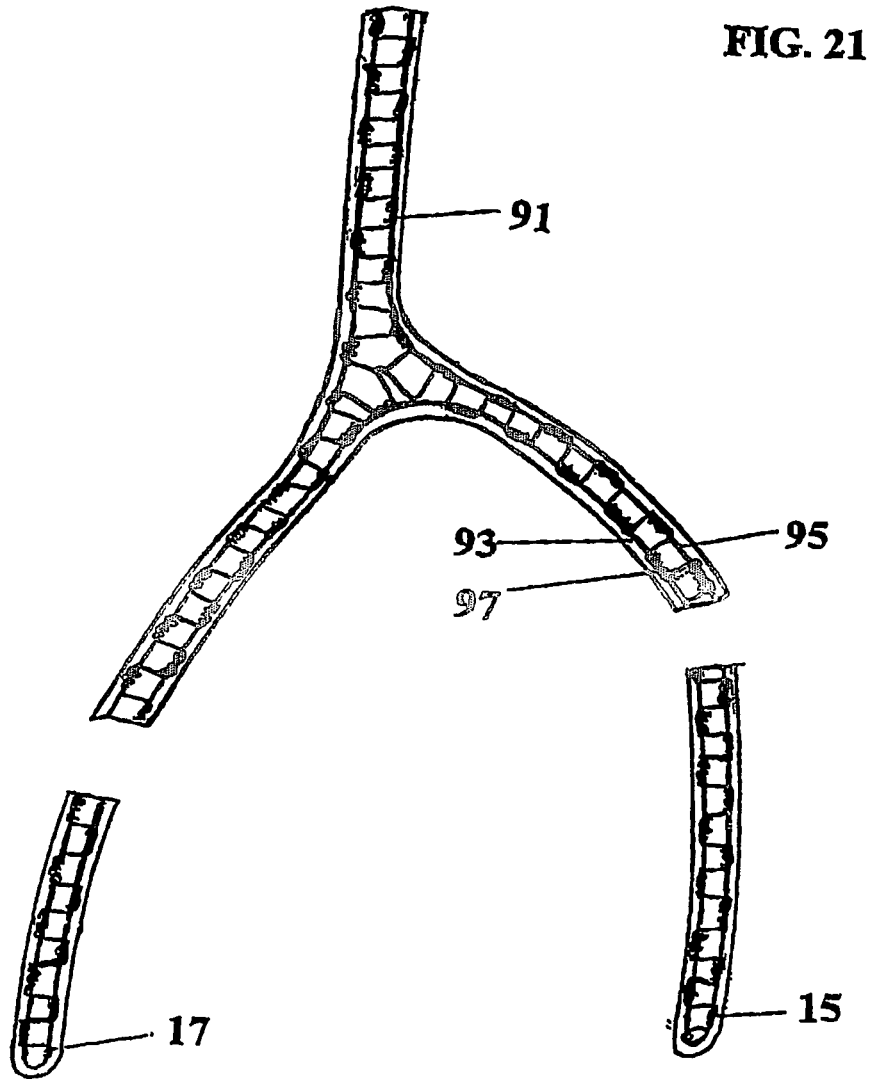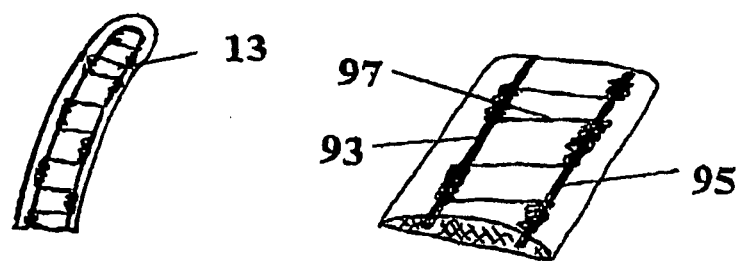
FIG. 20
FIG. 21

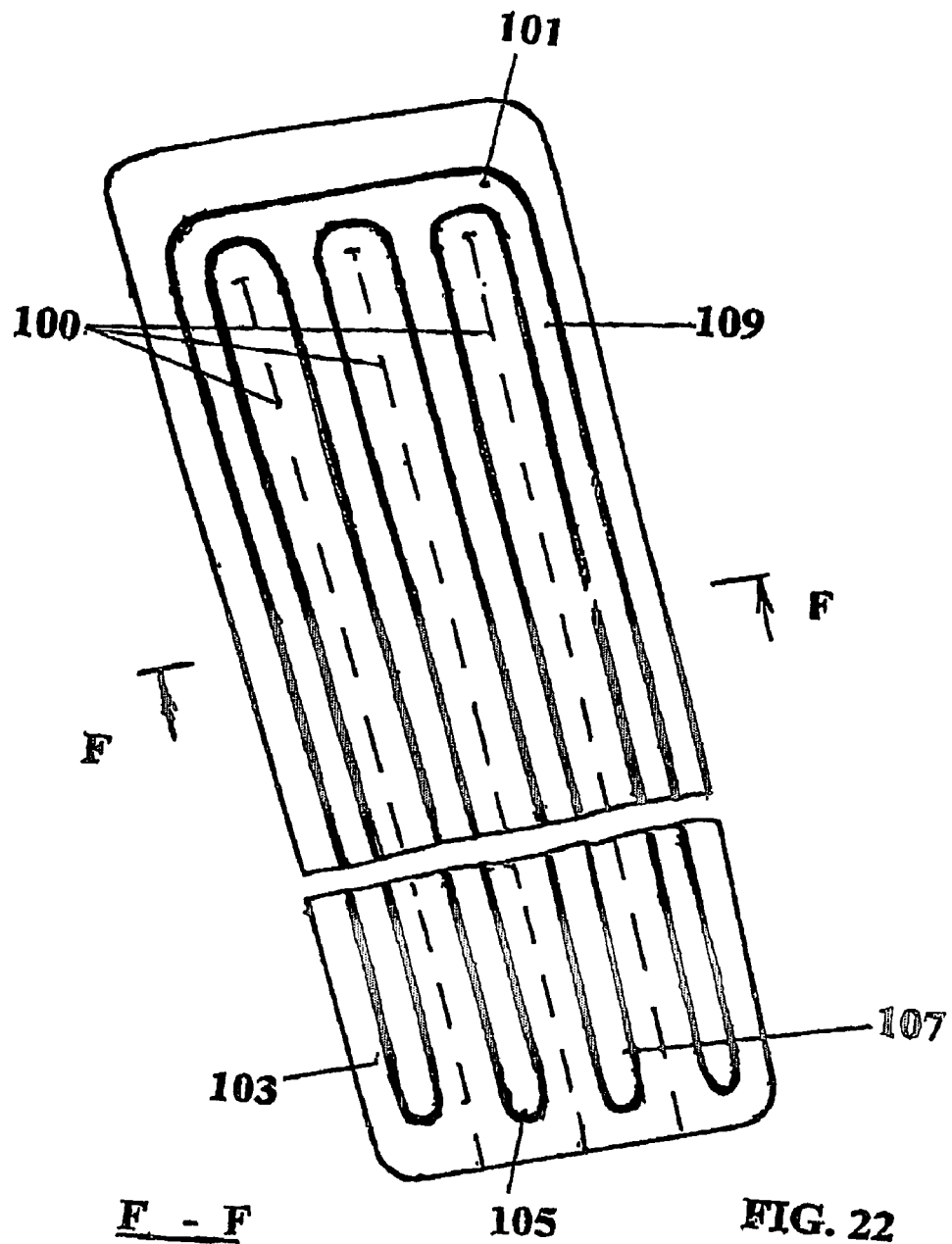
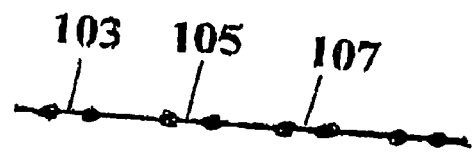
FIG. 23

** METHOD AND EXTRAVENOUS CORRECTOR FOR SIMULTANEOUS REPAIR OF MULTIPLE INCOMPETENT VALVES

FIELD OF THE INVENTION

The present invention relates to a method and device for repairing incompetent venous valves and more specifically relates to repair method and an implantable support device which is positionable about a dilated veins of the Sapheno-Femoral Junction (SFJ) with the aim to apply an external compression force on the insufficient veins of SFJ and especially in the area of the venous valves. These forces tend to reapproaching of the valves' leaflets and bring them closer to each other. Generally this forces is perpendicular to the edges of the valve cusps, tensioning the cusp edges and bringing the valve edges into apposition to restore their competence.

BACKGROUND OF THE INVENTION

Varicose veins in lower limbs is one of the most common vascular diseases. Venous valves in humans are normally bicuspid valves in which each valve cusp forms a reservoir for blood under pressure which forces the free edges of the cusps together to prevent reflux. Incompetence is a condition in which the cusps do not properly approach each other when a pressure differential or gradient is applied across a valve permitting reflux or retrograde flow of blood to occur. Medical literature indicates that many physicians believe that chronic venous insufficiency (CVI) of the lower limbs is the result of deep venous thrombosis (DVT) with associated inflammatory changes of venous valve cusps. Varicose veins often occur in the long saphenous veins in the medial part of the legs when valve incompetence occurs. A varicose vein is considered to be a condition which occurs when a vein dilates and the tributaries become elongated and tortuous, resulting in cosmetic impairment, inflammatory phlebitis, pain and thrombosis.

When the valves of the varicose, long saphenous vein are examined, changes are evident including dilation, evagination between the cusps, and in later stages the membrane between the commissures become thin and may have numerous fenestrae. These conditions are generally termed venous valve incompetence.

One of the most frequent symptoms of incompetence is poor coaptation of the valve cusps due to floppiness of the leading edges of the valve cusps. Reflux of blood flow occurs both along the free edges of the cusps and in the corneal areas.

Venous valve reconstruction has progressed to the point that competence can be achieved by both internal and external repair techniques.

In most cases varicose veins in lower limbs occurs due to insufficiency of the SFJ. In different countries of the World, on the average, from 40% to 60% of the female population over age 40 are affected by lower limb varicosity. It is also very important to save these veins for potential application thereof in aorto-coronary bypass or peripheral arterial reconstructions.

So far no efficient methods have been developed for the elimination of valve incompetence (insufficiency) and saving the superficial and deep veins, especially in the SFJ area. One of the surgical procedures to address this problem is application of sutures to the edges of the valve cusp leaflets in the corneal areas. The sutures are then pulled back and tied to the walls of the vein in order to reduce the length of the coapting edges of the leaflets. For example, the "Atlas of Venous Surgery (1992), at page 125, discusses various valve reconstruction techniques for primary valve insufficiency. One technique is entitled "Internal Technique by Transvalvular Venotomy" involves first laying open the valve by performing a venotomy to expose the valve. The object of the repair is to shorten the leading edge of each cusp to restore a cup-like configuration to both cusps in a procedure termed internal valvuloplasty. The valve is repaired with monofilament sutures at three locations (medial, lateral and posterior) until the leading edges of two valves lie gently across the face of the vein with the floppy, rugal folds eliminated.

The simplest and most effective solution of the problem is an external compression of the veins around the incompetent valves by extravenous corrector to reduce their central opening lumen and to restore valves function.

There are many engineering solutions applied in medicine for correcting defects in blood vessels and human hollow organs.

Devices and methods are known for reconstructions of effected blood vessels (U.S. Pat. No. 5,100,422 or "Venous Disorders" by John B. BERGAN and James S. T. YAO, W.B. Saunders Company, Philadelphia, 1991, p. 303-311).

Devices are also known for compression of vessels or hollow organs or securing portable medical instruments thereon (U.S. Pat. Nos. 5,160,338; 5,080,095; 5,171,252 or 4,938,765).

Such devices can compress the vein around the incompetent valve and control, within certain limits, the compression force. However, these devices cannot be disposed directly on a venous junction, and they do not provide the desired accuracy in compression rate control.

Special devices are further known for occuring the vein (U.S. Pat. Nos. 4,586,501 or 4,531,519) applied in surgery. They provide a more accurate control of the vein compression rate. However, they cannot be secured directly on the venous junction. Besides, they are complex in design (with a remote pressure source) and relatively large-sized, so they cannot constantly and independently operate inside the human body.

Most similar to the present invention in the device disclosed in U.S. Pat. No. 5,120,300 and in the book "Plastic and reconstructive operations on great veins", by A. N. Vedensky, "Medizina", Leningrad, 1979, p. 186-194. Such devices comprise bands (U.S. Pat. No. 5,120,300) or spiral springs formed of plastic, metal, alloy or plastic reinforced with metal (lavsan, fluorineplastic etc.).

The common drawback of all devices described above is follows: they cannot be applied for correction of vein valves, disposed in the venous junctions.

THE PRIOR ART

In U.S. Pat. No. 5,147,389 describes a cuff for restoring competence to an incompetent venous valve consists of a band of biocompatible implantable material that is not stretchable at blood flow pressures. The band is of sufficient length to encompass the vein at the site of the venous valve with the ends of the band overlapping. The cuff is placed around the vein at the site of the valve and the circumference of the cuff (and hence the diameter of the vein at the valve site) is reduced until competency of the valve in the vein is restored.

A method of extravascular correction of the function of incompetent vein valves and an extravascular corrector described in WO 09638090A1. The method consists of exposing the affected section of vein, mobilising it in the region around the incompetent valve and constructing the lumen of the vein using the corrector attached to the vein in the region of the incompetent valve. The material used for the corrector outer frame is an extremely resilient shape-memory alloy (titanium/nickel). The outer frame of the corrector is in the form of a hollow elliptical cylinder can be helical or sinusoidal and made from a wire or a sheet perforated in a particular way.

It is known also an implantable support device for restoring competence to venous valves (WO 9740755A1, EP 898463A1, AU 2817097A1, CA 02252894AA, etc). The device has opposed compression member of a biocompatible material, which is incorporates a reinforcing or spring-like member such as stainless steel wire. The device is applied externally about a vein at an incompetent venous valve site which device serves to flatten or compress but not occlude the vein. Flattening is induced generally normal to the coapting edges of the valve cusps restoring the competence of the valve by causing an elongating tension to be applied to the free edges of the cusps to bring them into apposition.

The common drawbacks of all described above devices and methods are as follows:
1) they cannot be applied for correction of vein valves, disposed in at least two veins of the said venous junctions;
2) they have only a compressing portion whereas no fixing means is provided to prevent axial displacement of the compressing member along the vein.

The most similar to the present invention is a compression device and method for external correction of insufficient valves in venous junction, describe in U.S. Pat. No. 5,476,471. The compression device, which adapted for placement around the junction, has a band encompassing at least two veins of these junction. The band has different rigidity and compression force in a direction extending from its proximal end to its distal end. The band is formed with a main compression portion disposed on a vein surface of the junction around an insufficient valve. Intermediate and fastening portions of the band are also disposed on the vein surfaces adjacent the main compressing portion. The band is preferably shaped as a Mobius band.

However, this device and method present a complicated, relatively expensive and not adequately technological design of the implanted device. Besides, it is not sufficiently adapted for placement on venous junctions of various shapes. The placement of the device is a relatively long procedure, and the fixation of the fastening portion is inconvenient.

An object of the present invention is to provide a most simple, cheap and technologically easy device and method for a controlled correction of an incompetent valve immediately in the venous junction, and, if necessary, of the incompetent valve in the area adjoining said junction.

SUMMARY OF THE INVENTION

An object of the present invention is a method and device—an extravenous corrector, for simultaneous repair of multiple incompetent venous valves in venous junctions. The device is adapted for placement substantially around the junction with insufficient valves in abutting contact with a desired area of junction.

The extravenous corrector comprises a central support member adapted to be placed on the surface of veins converging to the center of a venous junction, as well as at least three lengths of a band connected to it and adapted to be placed around at least two veins of the venous junction in the area of location of insufficient valves. These lengths of band possess different rigidity and compressing force in direction from their proximal end to distal end.

The central support member of the claimed extravenous corrector is, in top view, shaped as a flat rounded geometrical figure; circle, ellipse or polygon with rounded angles. Besides, the central support member may have in the middle a lightened area formed at least as one hole or at least one bulge.

Each of the band lengths may be a separate element attachable to the central support member. At least one of the band lengths may be shaped as a Mobius band.

The extravenous corrector may further be formed from a thin, flexible sheet of biologically compatible metal or alloy, chosen from a group comprising stainless steel, titanium, tantalum, nickel, zirconium, niobium, alloys of titanium and tantalum, nitinol. In this case, the central support member and at least three band lengths connected to it may be perforated, with through holes and rounded edges.

Each of the band lengths of the extravenous corrector may have uneven thickness, a thinned perforated middle and thickened rounded edges, and the holes in the middle of band are through, with rounded edges.

Each of the band lengths of extravenous corrector may be also formed as a separate element rigidly or pivotally attachable to the central support member. In this case, in particular, the central support member may be formed as a pivot to which at least three band lengths are pivotally attached.

The central support member and at least three band lengths connected to the latter may be coated with plastic. The plastic is chosen from a group comprising polytetrafluoroethylene, porous polytetrafluoroethylene, fluorinated ethylene propylene, perfluoro alkoxy, polyethylene therephthalate, polyurethane, absorbable polymers and resorbable polymers.

The extravenous corrector for simultaneous repair of incompetent valves in venous junctions may be also formed as a plastic coated thin, flexible wire from biologically compatible metal or alloy chosen from a group comprising stainless steel, titanium, tantalum, nickel, zirconium, niobium, alloys of titanium and, nitinol. In this case, each of the band three lengths is formed by at least two parallel lengths of thin, flexible wire coated with plastic. In another embodiment, each of the three band lengths is formed as a woven net structure containing at least two parallel lengths of thin, flexible wire interlaced with a third length of wire. In this case, the third length of wire may have substantially a smaller diameter than the first two lengths.

As in the above embodiment, the central support member is, in top view, shaped as a flat, rounded geometrical figure: circle, ellipse or polygon with rounded angles. The central support member may have in the middle a lightened area formed as at least one hole or at least one bulge. At least one of the band lengths may be shaped as a Mobius band.

As in the preceding embodiment, each of the band lengths may be formed as a separate element, rigidly or pivotally attachable to the central support member. The central support member may be formed as a joint, to which at least three aforesaid band lengths are pivotally attached.

The central support member and at least three band lengths attached to it are coated with plastic chosen from a group comprising polytetrafluoroethylene, porous polytetrafluoroethylene, fluorinated ethylene propylene, perfluoro alkoxy, polyethylene therephthalate, polyurethane, absorbable polymers and resorbable polymers.

Finally, the extravenous corrector may comprise a central support member and at least three band lengths connected to it which are coated with plastic and formed as a single length of a multicore flat cable.

There is also proposed a method for simultaneous repair of multiple incompetent venous valves in venous junctions comprising several successive steps.

At the first stage, surgical exposure of the venous junction is performed. Then, the extravenous corrector is placed outside the venous junction in such a way that the central support member is disposed immediately on the junction, and the three bands lengths wrap and wind around corresponding veins of the junction. Then, blood reflux is determined in one of the veins with incompetent valve. Thereupon, there is performed gradual compression of this vein until the reflux disappears, by changing the coiling force of the respective first band length. Next, the effect is checked, and, if necessary, the step is repeated by increasing or reducing compression via rewinding the respective first band length and fixating its free end.

Then the second step is performed—determining a need for adjusting reflux in the next vein, and, if necessary, repeating the procedure with the second band length, checking reflux in the second venous valve with following fixation of the free end of second band length, adjusting the compression rate and the length of second band length by cutting off a redundant piece of same.

Then comes the third step—determining a need for adjusting reflux of still another vein, repeating procedures with the third band length, checking reflux in the third venous valve with following fixation of the free end of third band length, adjusting compression rate and length of third band length by cutting off a redundant piece of same. In the course of correcting insufficient veins at least one of the band lengths may be wound, as a Mobius band, on the surface of a corresponding vein.

If placement of the third and following band lengths is not necessary, these lengths are entirely cut off.

Finally, there is performed checking of final correction effect by determining blood reflux in the corrected venous junctions a whole and closing the junction by routine technique. In the course of correcting insufficient veins with incompetent valves, at least one of the band lengths may be wound, as a Mobius band, on the surface of a corresponding vein.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

The invention will now be described in conjunction with the following drawings in which like reference numerals designate like elements and wherein:

FIG. 4-6 is a general view of the most preferred embodiment of the proposed extravenous corrector;

FIG. 13-15 is an embodiment of the proposed extravenous corrector formed as a connection of several parts, as well as cross sections of the central support member (FIG. 14) and one of peripheral portions (FIG. 15);

FIG. 16-18 is an embodiment of the proposed extravenous corrector as an articulation of several parts, as well as cross sections of one of the peripheral portions (FIG. 17) and central support member (FIG. 18);

FIG. 20-21 is an embodiment of the proposed extravenous corrector comprising a woven net structure, as well an enlarged fragment of one of its peripheral portions (FIG. 21);

FIG. 22-23 is an embodiment of the claimed extravenous corrector as a cable (a wire structure coated with plastic), and its cross section (FIG. 23).

DETAILED DESCRIPTION OF THE INVENTION

Below is a description of the most preferred embodiments of the claimed invention. As may be seen from embodiments presented in this description, the invention can solve the problem of eliminating valve incompetency in venous junctions (SFJ). Thus, it is intended that the present invention cover the modifications and variations of the invention, provided they come within the scope of the appended claims and their equivalents.

Figure 1:
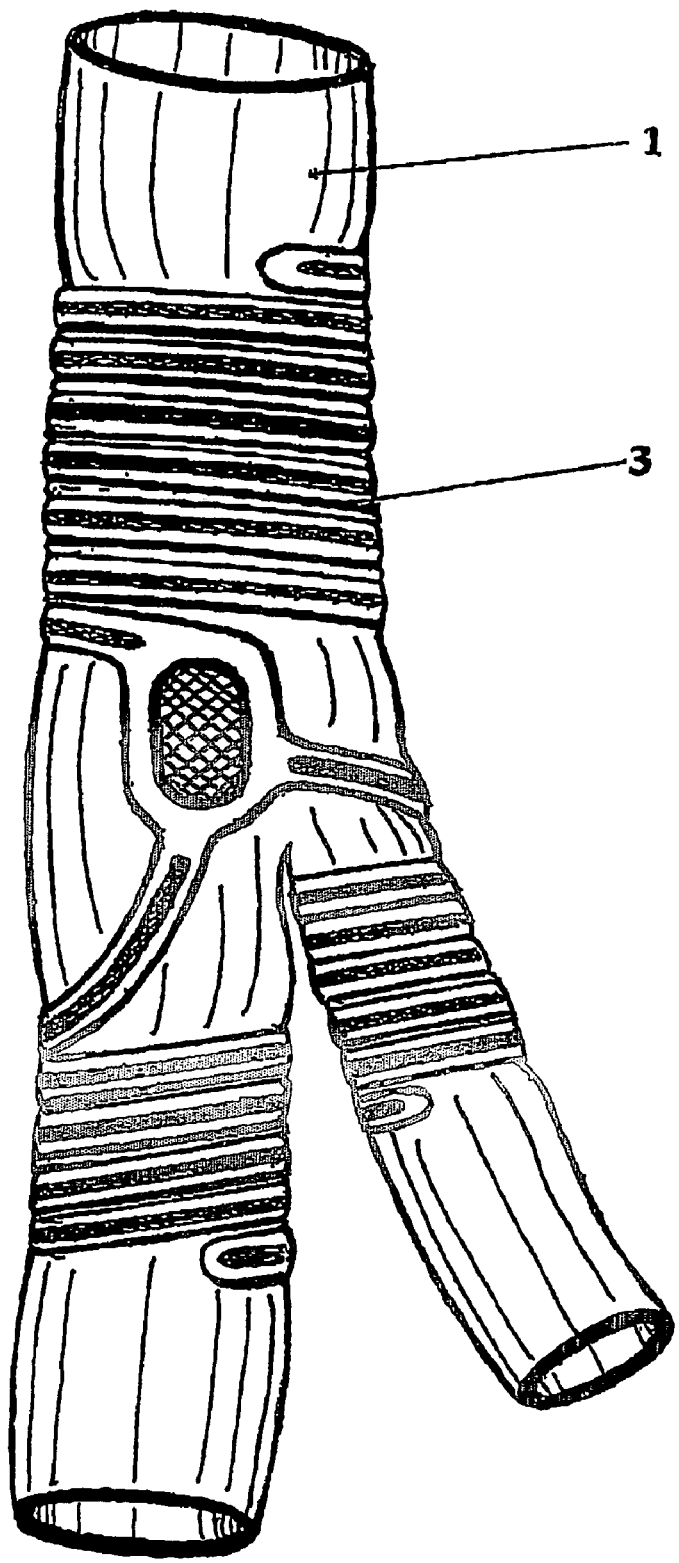
FIG. 1 is a general view of the most preferred embodiment of the proposed extravenous corrector placed on the surface of a venous junction.

FIG. 1 is a general view of a venous junction 1 with the claimed extravenous corrector 3 in the most preferred embodiment placed on the surface of the device.

Figure 2:
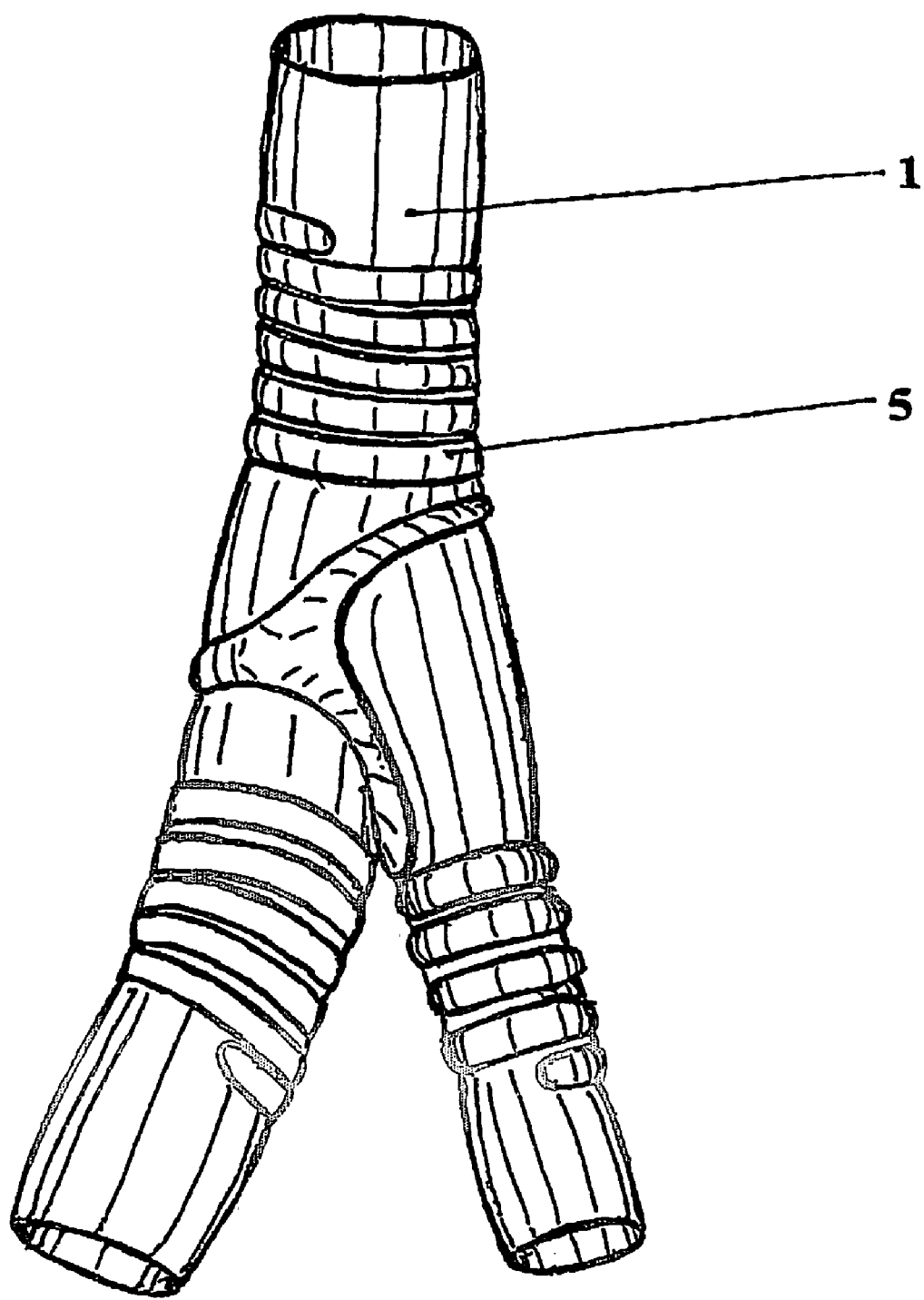
FIG. 2 is a general view of a second preferred embodiment of the proposed extravenous corrector placed on the surface of a venous junction.

FIG. 2 is a general view of a venous junction (SFJ) 1, on the surface whereof there is placed the claimed extravenous corrector 5 in the second preferred embodiment.

Figure 3:
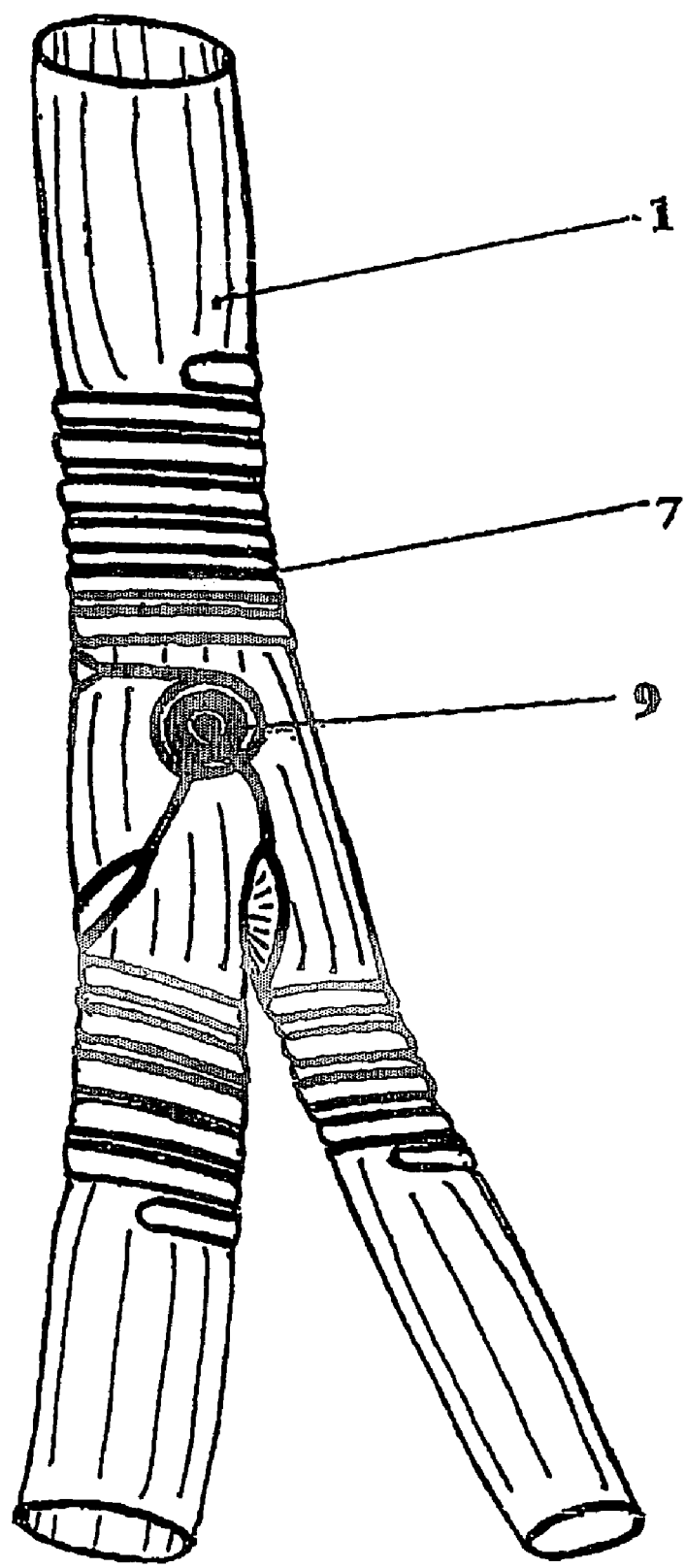
FIG. 3 is a general view of a third preferred embodiment of the proposed extravenous corrector placed on the surface of a venous junction.
Figure 7:
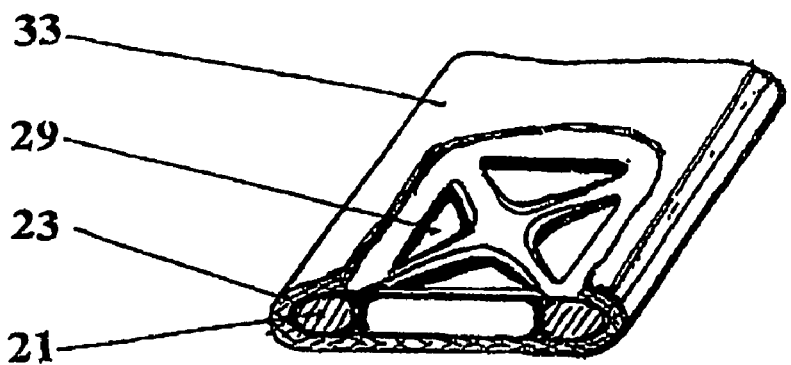
FIG. 7-10 are versions of cross section of peripheral portions of the proposed extravenous corrector.
Figure 8:
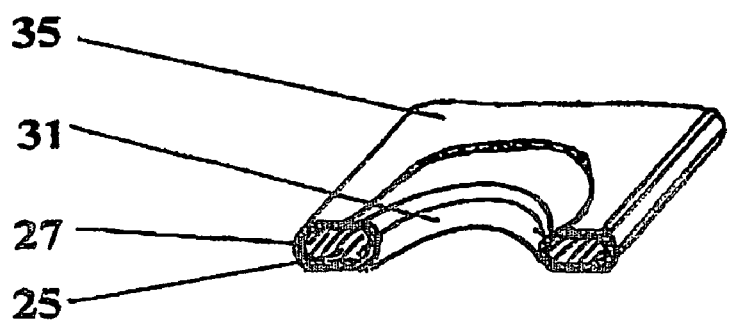
Figure 9:
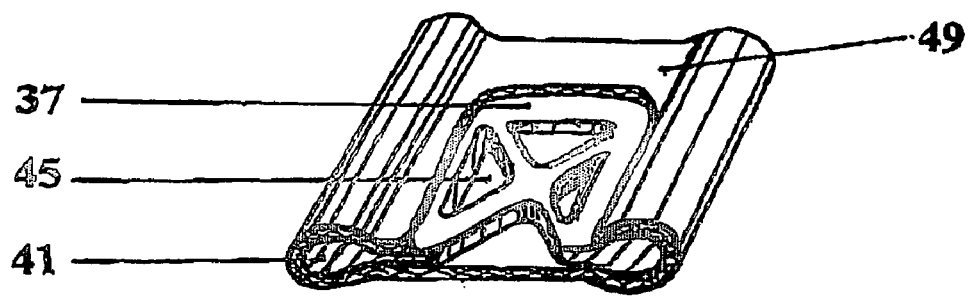
Figure 10:
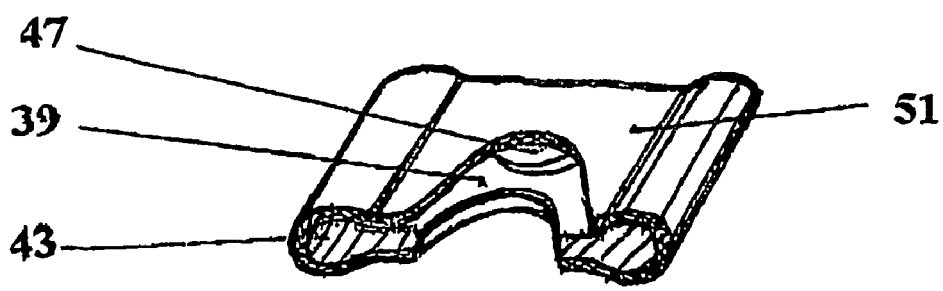
Figures 11, 12:
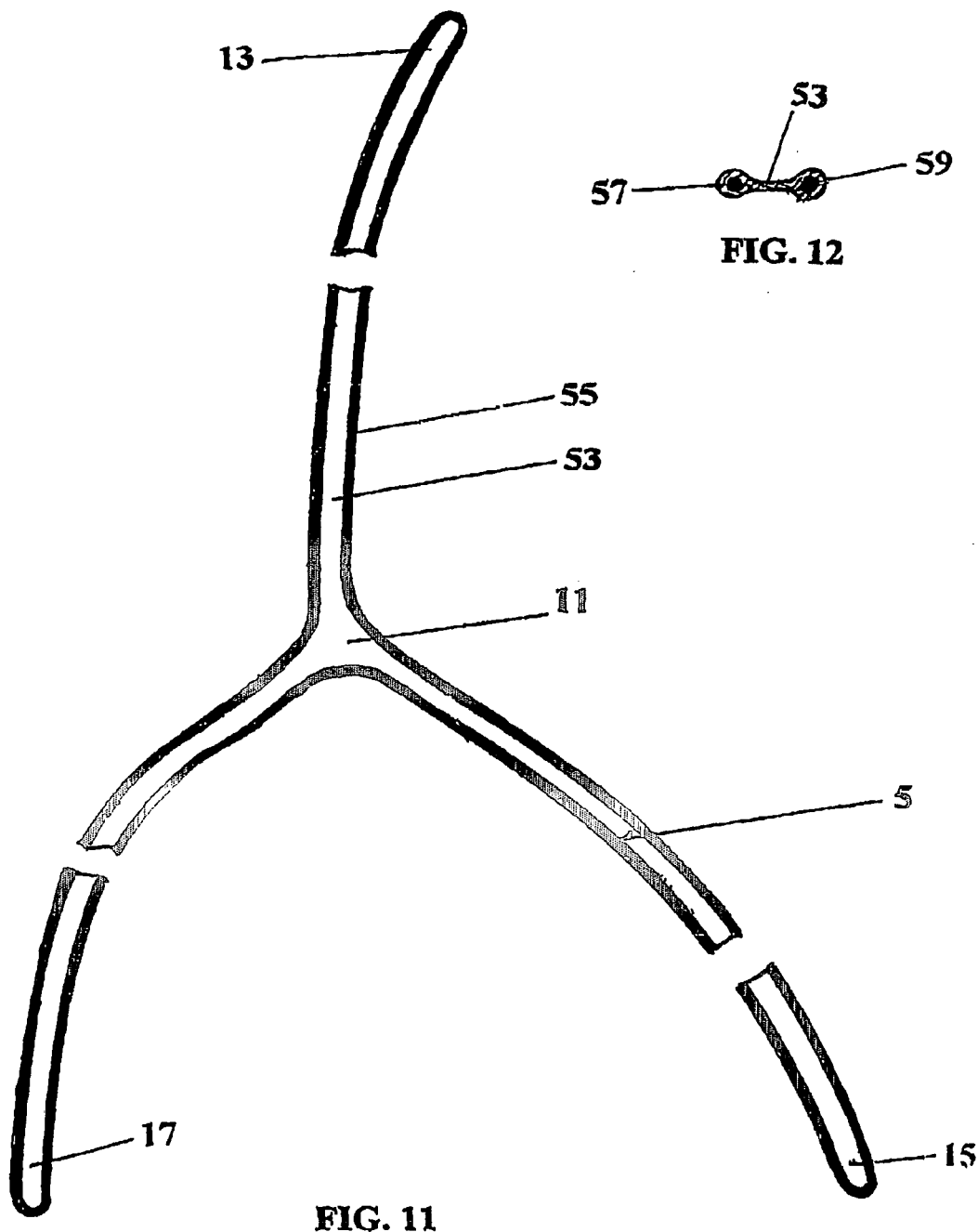
FIG. 11-12 is a general view of the second preferred embodiment of the proposed extravenous corrector and cross section of its peripheral portion.

And finally, FIG. 3 is a general view of a venous junction (SFJ) 1, on the surface whereof there is placed the claimed extravenous corrector 7 in its third preferred embodiment (with elements connected together via a joint 9).

Extravenous corrector 3 (FIG. 4-6, FIG. 1) comprises a central support member 11 adapted to be disposed on the surface of converging veins in the center of SFJ (FIG. 1), and at least three band lengths 13, 15 and 17, connected with it and adapted to be disposed around at least two veins of venous junction 1 in the area of location of incompetent valves. These band lengths 13, 15 and 17 possessing different rigidity and compressing force in direction from their proximal to distal end. Central support member 11 of the claimed extravenous corrector 3 (see FIG. 1) is shaped, in its top view, as a flat rounded geometrical figure, in this case, substantially as an ellipse. It may be as well shaped as a circle or polygon with rounded angles. Besides, central support member 11 has in its middle a lightened portion shaped as a mesh 19, which may be as well shaped as at least one hole or at least one bulge (not shown in the drawings).

Each of the band lengths 13, 15 and 17 may be formed integral with central support member 11 (FIG. 4). At the same time, each of the band lengths 13, 15 or 17 may be a separate element, rigidly or pivotally attachable to central support member 11 (FIG. 13). In this case, particularly, central support member 11 may be shaped as a pivot to which there are pivotally attached at least three band lengths 13, 15 or 17.

In both said embodiments at least one of the band lengths 13, 15 or 17 may be shaped as a Mobius band (FIG. 3).

In the first, most preferred embodiment (FIG. 6-10), the extravenous corrector 3 is formed of thin, flexible sheet of a biologically compatible metal or alloy, chosen from a group comprising stainless steel, titanium, tantalum, nickel, zirconium, niobium, alloys of titanium and tantalum, nitinol. In this case central support member 11 and at least three band lengths 13, 15 or 17 connected to it may be perforated, with through holes with rounded edges. Holes 19 in central support member 11 may be round, square, triangular (FIG. 4) or have another shape.

Each of band lengths 13, 15, 17 of extravenous corrector 3 may have even thickness (see FIG. 7, 8), be formed of a matal band 21 or 25 with rounded edges, 23 and 27, respectively, and with triangular 29 or round 31 holes in the middle, also having rounded edges. In this case, band lengths 13, 15 and 17 are coated with a layer of plastic, 33 and 35 respectively.

Besides, each of the band lengths 13, 15, 17 of extravenous corrector 3 may have uneven thickness (FIG. 9, 10), a lightened perforated middle, 37 and 39 respectively and with thickened rounded edges, 41 and 43, and the holes, respectively 45 and 47, in the band middle are through, with rounded edges. In these embodiments band lengths 13, 15 and 17 are as well coated with a plastic layer, 49 and 51 respectively.

In the described embodiment of extravenous corrector 3 the central support device 11 and at least three band lengths 13,15, or 17 connected to it may be coated with plastic chosen from a group comprising polytetrafluoroethylene, porous polytetrafluoroethylene, fluorinated ethylene propylene, perfluoro alkoxy, polyethylene therephtalate, polyurethane, absorbable polymers and resorbable polymers.

FIG. 11-18 show the second embodiment of extravenous corrector 5 for external correction of incompetent valves in venous junctions 1 comprising a thin, flexible wire 55 from a biologically compatible metal or alloy, chosen from a group including stainless steel, titanium, tantalum, nickel, zirconium, niobium, alloys of titanium and tantalum, nitinol, the wire being coated with plastic 53. In this case each of three band lengths 13, 15 or 17 contains at least two parallel lengths 57 and 59 of thin, flexible wire 55 coated with plastic 53 (FIG. 12), which is, as in the previous embodiment, chosen from a group including polytetra-fluoroethylene, fluorinated ethylene propylene, perfluoro alkoxy, polyethylene therephtalate, polyurethane, absorbable polymers and resorbable polymers.

As in the previous embodiment, central support member 11 is shaped, in top view, as a flat geometrical figure: circle, ellipse or polygon with rounded angles. The central support member 11 in this embodiment may as well have in its middle a lightened portion having at least one hole or at least one bulge. In this case at least one of band lengths 13, 15 or 17 may be shaped as a Mobius band.

As in the above embodiment, each of band lengths 13 15 or 17 may by formed as a separate element 61, 63, 65, rigidly or pivotally attachable to central support member 11 (FIG. 13-15). In this case central support member 11 may be shaped as a separate element 67 (FIG. 13-15) with holes 69.

Figure 19:
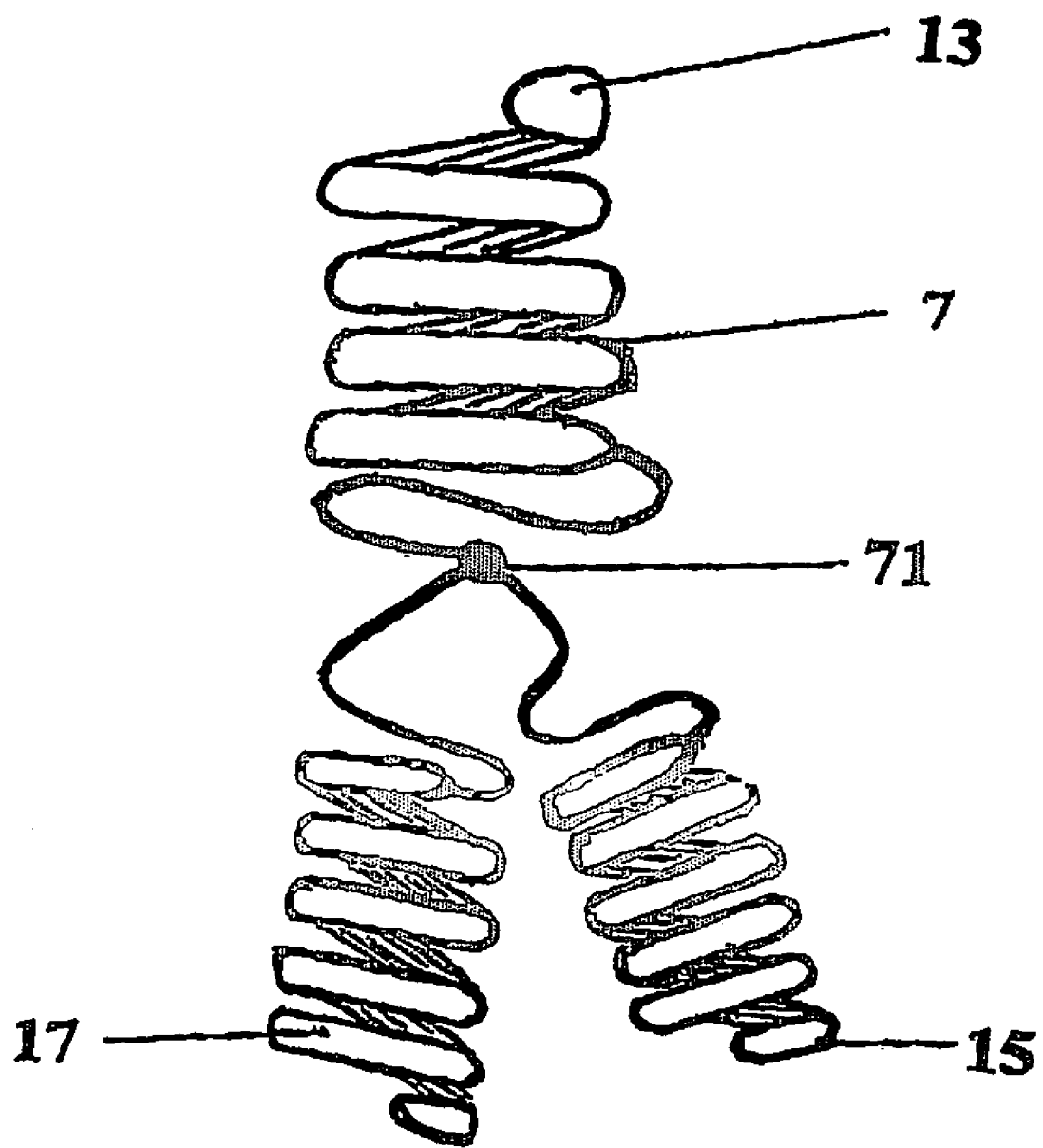
FIG. 19 is a three-dimensional position of the proposed extravenous corrector comprising a rigid or pivotal connection of several parts.

FIGS. 3 and 16-18 show an embodiment of an extravenous corrector 7 with central support member 11 shaped as a joint 71, to which there are pivotally attached three band lengths 13, 15, 17 formed as separate elements 73, 75 and 77. In this case separate elements 73, 75 and 77 contain one band length 79, which is then divided into two parallel lengths 81 and 83 (FIG. 16-18). All these separate elements from wire lengths 79, 81 and 83 are coated with plastic 85 (see FIG. 16), which, as in the above embodiments of the compression device, is chosen from a group, including polytetrafluoroethylene, porous polytetrafluoroethilene, fluorinated ethylene propylene, perfluoro alkoxy, polyethylene therephthalate, polyurethane, absorbable polymers and resorbable polymers. On FIG. 19 is a three-dimensional view of extravenous corrector 7, according to its present embodiment.

FIG. 20, 21 show an embodiment of the claimed extravenous corrector, wherein each of three band lengths 13, 15 and 17 is shaped as a plastic coated woven net structure 91, containing at least two parallel lengths 93 and 95 of thin, flexible wire, interlaced with a third band length 97 (see FIG. 21, 20). In this case band length 97 may have a substantially smaller diameter than the first two lengths (see FIG. 21). The woven net structure 91 is coated with the same plastic as in the above embodiments.

Finally, FIG. 22, 23 show an embodiment of extravenous corrector wherein central support member 101 and at least three band lengths 103, 105 and 107 connected to it, are coated with plastic and shaped as a single length of a multi-core cable 109. Cable 109 is coated with the same plastic that is used in the above embodiments of extravenous corrector, the three band lengths 103, 105 and 107 being separated from cable 109 by cutting it along its longitudinal axis over a desired length.

The claimed embodiments of the extravenous corrector may be applied on the basis of the claimed method for simultaneous repair of multiple incompetent venous valves in venous junctions 1, the method comprising several successive steps. Let us consider the implementing of this method via the most preferred embodiment of extravenous corrector 3, shown in FIGS. 1 and 5-10.

In the first step there is surgically disposed the venous junction. Then the extravenous corrector 3 is placed outside venous junction 1 in such a way, that central support member 11 is located immediately on junction 1, and three band lengths 13, 15 and 17 wrap and wind around the corresponding veins of junction 1. Then blood reflux is determined in one of the veins with an incompetent valve. Next, there is performed gradual compression of this vein until the reflux disappears, by changing the force of coiling the corresponding band length, such as 13. Further, the effect is checked, and, if necessary, the operation is repeated, increasing or reducing compression force via rewinding the corresponding first band length 13 and fixating its free end.

Then the second step is performed—determining a need for adjusting the reflux of the following vein and, if necessary, repeating the operations with the second band length 15, checking the reflux in the second venous valve with following fixation of the free end of the second band length 15, adjusting compression rate and length of the second band length 15 by cutting off its redundant portion.

Thereafter the third step is performed—determining a need for adjusting one more vein, repeating the operations with the third band length 17, checking the reflux in the third venous valve with following fixation of the free end of third band length 17, adjusting compression rate and length of third band length 17 by cutting off its abundant portion. In the course of correcting insufficient veins, at least one of band lengths 13, 15 or 17 may be coiled as a Mobius band on the surface of a corresponding vein.

When the placement of a third, fourth or following band lengths is not necessary, these lengths are completely cut off.

At last, final correction effect is checked by determining blood reflux in the whole corrected junction 1, and the junction is closed by routine technique. In the course of correcting venous insufficiency, at least one of band lengths 13, 15 or 17 may be coiled as a Mobius band on the surface of the corresponding vein.

The claimed method for simultaneous repair of multiple incompetent valves in venous junctions 1 is performed in a similar way when other embodiments of extravenous corrector are applied.

As a whole, the application of the claimed implanted extravenous corrector manufactured according to the described embodiments, makes same simple, cheap and technologically efficient, as well as more adapted for being placed on venous junctions of diverse shapes. Moreover, the time for the corrector placement is reduced, and fixating of fastening portion of the extravenous corrector becomes more convenient.

It should be understood that while the above is a complete description of the preferred embodiments of the invention, various alternatives, modifications and equivalents may be used. Therefore, the above description should not be taken as limiting the scope of the invention which is defined by the following claims.

The invention claimed is:

1. An extravenous corrector for external correction of multiple insufficient valves in venous junctions, said corrector being adapted for placement substantially around the junction with said multiple incompetent valves in abutting contact with a desired area of said junction, said extravenous corrector comprising:
   a central support member adapted for placement on a surface of converging veins in a center of a venous junction, and
   at least three band lengths connected to said central support member and extending therefrom, the at least three bands adapted for placement around at least two veins of said venous junction in the area of location of their respective incompetent valves, said at least three band lengths each possessing different rigidity and being adapted to exert an adjustable compressing force in a direction extending from a proximal end to a distal end thereof,
   the corrector being adapted to apply an external force to at least two veins near the venous junction, each band length acting substantially normally towards a center of a corresponding vein and being capable of generating a force sufficient to restore union and sufficiency of a corresponding venous valve, said at least three band lengths being adapted to be wrapped and wound around corresponding veins of the junction.

2. An extravenous corrector according to claim 1 wherein said central support member is shaped, in its top view, as a flat rounded geometrical figure: circle, ellipse, or polygon with rounded angles.

3. An extravenous corrector according to claim 1 wherein said central support member has, in a middle thereof, a lightened portion having at least one hole with rounded edges.

4. An extravenous corrector according to claim 1 wherein said central support member has, in a middle thereof, a lightened portion shaped as at least one bulge.

5. An extravenous corrector according to claim 1 wherein at least one of said band lengths is shaped as a Mobius band.

6. An extravenous corrector according to claim 1 wherein each of said band lengths is formed as a separate element, attachable to said central support member.

7. An extravenous corrector according to claim 6 wherein each of said band lengths is rigidly or pivotally attachable to said central support member.

8. An extravenous corrector according to claim 1 wherein said corrector is formed of a thin flexible sheet made of a biologically compatible metal or alloy selected from the group consisting of stainless steel, titanium, tantalum, nickel, zirconium, niobium, alloys of titanium and tantalum, nitinol.

9. An extravenous corrector according to claim 1, wherein said central support member and said at least three band lengths, connected to said member, are perforated, with through holes having rounded edges.

10. An extravenous corrector according to claim 1 wherein said at least three band lengths have uneven thickness, a thinned perforated middle and thickened rounded edges, holes in the band middle being through holes with rounded edges.

11. An extravenous corrector according to claim 1, wherein said central support member and said at least three band lengths connected to said member are coated with plastic.

12. An extravenous corrector according to claim 11, wherein said central support member and said at least three band lengths connected to said member, are coated with biologically compatible plastic, chosen from a group including polytetrafluoroethylene, porous polytetrafluoroethylene, fluorinated ethylene propylene, perfluoro alkoxy, polyethylene therephthalate, polyurethane, absorbable polymers and resorbable polymers.

13. An extravenous corrector according to claim 1 wherein said corrector is formed of a plastic-coated thin, flexible wire made from a biologically compatible metal or alloy.

14. An extravenous corrector according to claim 1 wherein said corrector is formed of a thin flexible wire made from a biologically compatible metal or alloy, chosen from a group including stainless steel, titanium, tantalum, nickel, zirconium, niobium, alloys of titanium and tantalum, nitinol.

15. An extravenous corrector according to claim 1, wherein said corrector is woven from a thin flexible wire coated with plastic.

16. An extravenous corrector according to claim 1, wherein each of said three band lengths is formed by at least by two parallel lengths of thin flexible wire coated with plastic.

17. An extravenous corrector according to claim 1, wherein each of said three band lengths has a plastic-coated woven net structure, having at least two parallel lengths of thin flexible wire interlaced with a third wire length.

18. An extravenous corrector according to claim 1, wherein each of said three band lengths has a plastic-coated woven net structure, having at least two parallel lengths of thin flexible wire interlaced with a third wire length with a substantially smaller diameter that that of the first two lengths.

19. An extravenous corrector according to claim 1, wherein said central support member and said at least three band lengths, connected to said central support member, are covered with plastic and shaped as a single length of a multicore flat cable.

20. A method for simultaneous repair of multiple incompetent venous valves in venous junctions, comprising the following successive steps:
   surgically exposing the venous junction;
   providing an extravenous corrector having:
   a central support member adapted for placement on a surface of converging veins in a center of a venous junction, and
   at least three band lengths connected to said central support member and extending therefrom, the at least three bands adapted for placement around at least two veins of said venous junction in the area of location of their respective incompetent valves, said at least three band lengths each possessing different rigidity and being adapted to exert an adjustable compressing force in a direction extending from a proximal end to a distal end thereof,
   the corrector being adapted to apply an external force to at least two veins near the venous junction, each band length acting substantially normally towards a center of a corresponding vein and generating a required constant force to restore union and sufficiency of a corresponding venous valve, said at least three band lengths being adapted to be wrapped and wound around corresponding veins of the junction;

placing the extravenous corrector outside the venous junction;

determining blood reflux in a first vein with an insufficient valve;

performing a gradual compression of the vein until the reflux disappears, by wrapping the first band length around the first vein and changing the force of coiling of the corresponding first band length;

checking the effect and, if necessary, repeating the procedure, by increasing or reducing compression via rewinding the first band length and fixating its free end;

determining a need for adjusting the reflux of a second vein;

repeating the procedures with the second band length, checking the reflux in the second venous valve with following fixation of the free end of said second band length, the compression rate and length of the second band length being adjusted by cutting off a redundant portion thereof;

determining if there is a need for adjusting reflux of a third vein;

repeating the procedures with the third band length, checking reflux in the third venous valve, adjusting compression rate and length of the third band length by cutting off a redundant portion thereof;

if there is no need for adjusting reflux of a third vein, cutting off the entire length of the third band length;

checking the final correction effect by determining the blood reflux in the entire venous junction being corrected, and closing the junction.

21. A method for simultaneous repair of multiple incompetent venous valves in venous junctions according to claim 20, wherein, in the course of correcting insufficient veins, at least one of said band lengths is coiled as a Mobius band on the surface of a corresponding vein.

* * * * *